US007019103B2

(12) United States Patent
Yokota et al.

(10) Patent No.: US 7,019,103 B2
(45) Date of Patent: Mar. 28, 2006

(54) POLYAMIC ACID OLIGOMER, POLYIMIDE OLIGOMER, SOLUTION COMPOSITION, AND FIBER-REINFORCED COMPOSITE MATERIAL

(75) Inventors: Rikio Yokota, Iruma (JP); Kohei Goto, Tsukuba (JP); Hideki Ozawa, Chiba (JP)

(73) Assignees: JSR Corporation, Tokyo (JP); Ube Industries, Ltd., Ube (JP)

( * ) Notice: Subject to any disclaimer, the term of this patent is extended or adjusted under 35 U.S.C. 154(b) by 0 days.

(21) Appl. No.: 10/838,244

(22) Filed: May 5, 2004

(65) Prior Publication Data
US 2005/0014925 A1 Jan. 20, 2005

(30) Foreign Application Priority Data
May 7, 2003 (JP) .............................. 2003-129115

(51) Int. Cl.
C08G 73/10 (2006.01)
C08G 69/26 (2006.01)
B32B 27/00 (2006.01)

(52) U.S. Cl. ...................... 528/170; 528/125; 528/126; 528/128; 528/172; 528/173; 528/176; 528/179; 528/183; 528/188; 528/220; 528/229; 528/350; 528/353; 525/420; 525/422; 428/411.1; 428/357; 428/394; 428/395; 428/396; 428/473.5

(58) Field of Classification Search ................ 528/170, 528/125, 126, 128, 172, 173, 176, 179, 183, 528/188, 220, 229, 350, 353; 525/420, 422, 525/432; 428/411.1, 357, 394, 395, 396, 428/473.5
See application file for complete search history.

(56) References Cited

U.S. PATENT DOCUMENTS

| 5,081,196 | A | * | 1/1992 | Yamamoto et al. ......... 525/419 |
| 5,109,105 | A | * | 4/1992 | Lubowitz et al. ........... 528/322 |
| 5,175,233 | A | * | 12/1992 | Lubowitz et al. ........... 528/170 |
| 5,260,412 | A | * | 11/1993 | Yamamoto et al. ......... 528/353 |
| 5,606,014 | A | * | 2/1997 | Connell et al. ............. 528/353 |
| 5,760,168 | A | * | 6/1998 | Hergenrother et al. ...... 528/353 |
| 5,817,744 | A | * | 10/1998 | Sheppard et al. ........... 528/353 |
| 6,129,982 | A | * | 10/2000 | Yamaguchi et al. ........ 428/336 |
| 6,281,323 | B1 | * | 8/2001 | Yokota et al. .............. 528/170 |
| 6,359,107 | B1 | | 3/2002 | Connell et al. |
| 6,808,818 | B1 | * | 10/2004 | Ozawa et al. ............ 428/473.5 |

FOREIGN PATENT DOCUMENTS

| JP | 6-32854 | 2/1994 |
| JP | 2000-53767 | 2/2000 |
| JP | 2000-219741 | 8/2000 |

OTHER PUBLICATIONS

J. A. Johnston, et al. "Synthesis and Characterization of Imide Oligomers End-Capped with 4-(Phenylethynyl)Phthalic Anhydrides", POLYMER, vol. 35, No. 22, 1994, pp. 4865-4873.

* cited by examiner

Primary Examiner—P. Hampton Hightower
(74) Attorney, Agent, or Firm—Oblon, Spivak, McClelland, Maier & Neustadt, P.C.

(57) ABSTRACT

A terminal-crosslinkable polyamic acid oligomer having 1) heat resistance indicated by Tg of 300° C. or more and a pyrolysis temperature of 500° C. or more, 2) toughness, and 3) capability of allowing an increase in concentration. The polyamic acid oligomer is obtained by reacting an aromatic tetracarboxylic dianhydride including 2,2',3,3'-biphenyltetracarboxylic dianhydride, an aromatic diamine compound, and a reactive crosslinking agent including an amino group or acid anhydride group and a crosslinkable group in the molecule, and includes a crosslinkable group at the molecular terminal.

11 Claims, No Drawings

US 7,019,103 B2

POLYAMIC ACID OLIGOMER, POLYIMIDE OLIGOMER, SOLUTION COMPOSITION, AND FIBER-REINFORCED COMPOSITE MATERIAL

Japanese Patent Application No. 2003-129115, filed on May 7, 2003, is hereby incorporated by reference in its entirety.

BACKGROUND OF THE INVENTION

The present invention relates to a terminal-crosslinkable polyimide oligomer obtained by reacting an aromatic tetracarboxylic dianhydride including 2,2',3,3'-biphenyltetracarboxylic dianhydride, an aromatic diamine compound, and a terminal-crosslinking agent. More particularly, the present invention relates to a polyamic acid oligomer and a polyimide oligomer useful as a molding material such as a matrix resin of a composite material used under a severe heat resistant environment, such as instruments for airplanes, space industries, and automobiles, and as a functional material such as an insulating material and a heat-resistant adhesive.

The present invention also relates to a solution composition of the polyamic acid oligomer and/or the polyimide oligomer, and to a fiber-reinforced composite material obtained from the polyamic acid oligomer and/or the polyimide oligomer.

A polyimide is known as a heat-resistant polymer material. Since the polyimide generally has an insoluble and infusible structure, a molded product is not necessarily obtained by thermal molding. The polyimide generally has excellent heat resistance, since the polyimide lacks melt moldability due to high melt viscosity even in a high temperature flow region because of high intermolecular interaction. If a flexible group is introduced into the molecular structure of a conventional polyimide or the concentration of the imide group is decreased in order to provide thermal moldability, physical heat resistance indicated by Tg tends to decrease. Specifically, thermal moldability and heat resistance of the polyimide have an inconsistent relationship.

However, a thermosetting polyimide can be provided with both thermal moldability and heat resistance. In more detail, a thermosetting polyimide can be provided with high-temperature flowability necessary for molding by selection of the monomer structure which reduces molecular interaction and oligomerization.

A crosslinkable group is introduced at the molecular terminal of the thermosetting polyimide. As the crosslinkable group, a maleimide structure, a propagyl structure, a phenylethynyl structure, and the like are known. A maleimide structure can be introduced at the molecular terminal of the polyimide oligomer by using a terminal-crosslinking agent such as maleic anhydride or nadic anhydride, for example.

A terminal-modified imide oligomer disclosed in Japanese Patent Application Laid-open No. 6-32854 is obtained by reacting 2,3,3',4'-biphenyltetracarboxylic dianhydride, an aromatic diamine compound, and a terminal-crosslinking agent including a group having an unsaturated bond represented by a maleimide structure.

In the case where the crosslinkable group has a phenylethynyl structure, the resulting crosslinked product has excellent heat resistance. In order to introduce a phenylethynyl structure at the molecular terminal of the polyimide oligomer, 4-(2-phenylethynyl)phthalic anhydride, 3-phenylethynylaniline, 3-ethynylaniline, or 4-ethynylaniline is used as the terminal-crosslinking agent, for example.

Polymer, vol. 35, p. 4865, 1994 discloses a terminal-modified imide oligomer and a thermally cured product in which a crosslinkable group having a phenylethynyl structure is introduced at the molecular terminal by reacting 4-(2-phenylethynyl)phthalic anhydride as a terminal-crosslinking agent with the molecular terminal of a polyimide precursor oligomer obtained from 2,2-bis(3,4-dicarboxyphenyl)hexafluoropropane dianhydride and p-phenylenediamine.

Japanese Patent Application Laid-open No. 2000-219741 discloses a terminal-modified imide oligomer and a thermally cured product in which a crosslinkable group is introduced at the molecular terminal by reacting 4-(2-phenylethynyl)phthalic anhydride as a terminal-crosslinking agent with the molecular terminal of an imide oligomer obtained from 2,3,3',4'-biphenyltetracarboxylic dianhydride and an aromatic diamine compound.

In the above thermally cured products, 1) improvement of heat resistance (improvement of Tg which indicates physical heat resistance and improvement of pyrolysis temperature which indicates chemical heat resistance, for example), 2) improvement of strength properties such as strength, modulus of elasticity, and toughness of the resulting cured product, and 3) an increase in the resin concentration during prepreging when producing a fiber-reinforced composite material using the terminal-modified imide oligomer in order to control the amount of resin in a prepreg and to obtain a molded product with a small number of defects are important. In particular, a decrease in the resin concentration during prepreging is caused by low solubility of the terminal-modified imide oligomer in an organic solvent due to the imide structure of the terminal-modified imide oligomer. A higher concentration solution in comparison with the polyimide may be obtained by using polyamic acid which exhibits higher solubility in an organic solvent than the polyimide. However, it becomes difficult to control the curing temperature due to formation of voids accompanying dehydration during imidization and generation of water having high latent heat of vaporization, whereby the resulting cured product becomes nonuniform. Moreover, since a high-concentration solution of polyamic acid is very unstable, storage stability is insufficient.

In the above thermally cured products, it is difficult to provide processability (high-temperature flowability and solubility, for example) and heat resistance, or strength properties (toughness) and heat resistance in combination.

BRIEF SUMMARY OF THE INVENTION

The present invention may provide a polyamic acid oligomer which exhibits 1) heat resistance (high Tg of 300° C. or more), 2) toughness, and 3) excellent solubility in a solvent and can be increased in concentration, and a polyimide oligomer obtained from the polyamic acid oligomer.

The present invention may also provide a solution composition of the polyamic acid oligomer and/or the polyimide oligomer, and a fiber-reinforced composite material obtained from the polyamic acid oligomer and/or the polyimide oligomer.

According to a first aspect of the present invention, there is provided a polyamic acid oligomer which is obtained by reacting an aromatic tetracarboxylic dianhydride including 2,2',3,3'-biphenyltetracarboxylic dianhydride, an aromatic diamine compound, and a terminal-crosslinking agent, and includes a crosslinkable group at a molecular terminal.

In the above polyamic acid oligomer, the aromatic tetracarboxylic dianhydride may further include 3,3',4,4'-biphenyltetracarboxylic dianhydride and/or 2,3,3',4'-biphenyltetracarboxylic dianhydride.

The polyamic acid oligomer may have a logarithmic viscosity ($\eta_{inh}$) (concentration: 0.5 g/dL, solvent: N-methylpyrrolidone (30° C.)) of 0.03 to 0.5 dL/g.

The polyamic acid oligomer may have a minimum melt viscosity of 10 to 100,000 poise.

In the polyamic acid oligomer, the terminal-crosslinking agent may be at least one compound selected from the group consisting of vinylaniline, aminostyrene, ethynylaniline, phenylethynylaniline, propargylamine, maleic anhydride, 5-norbornene-2,3-dicarboxylic anhydride, phthalic anhydride, and phenylethynylphthalic anhydride.

The polyamic acid oligomer may have a glass transition temperature of 300° C. or more and a flexural strength of 130 MPa or more after curing.

According to a second aspect of the present invention, there is provided a polyimide oligomer which is obtained by condensing the polyamic acid oligomer, the polyamic acid oligomer having a logarithmic viscosity ($\eta_{inh}$) (concentration: 0.5 g/dL, solvent: N-methylpyrrolidone (30° C.)) of 0.03 to 0.5 dL/g.

According to a third aspect of the present invention, there is provided a solution composition comprising the polyamic acid oligomer and/or the polyimide oligomer, and an organic solvent.

In the solution composition, the concentration of the polyamic acid oligomer and/or the polyimide oligomer may be 20 wt % or more.

According to a fourth aspect of the present invention, there is provided a fiber-reinforced composite material obtained by thermally curing a prepreg in which a fibrous reinforcement material is impregnated with an organic solvent solution of the polyamic acid oligomer and/or the polyimide oligomer.

In the fiber-reinforced composite material, the fibrous reinforcement material may be carbon fiber.

DETAILED DESCRIPTION OF THE EMBODIMENT

The present invention relates to a polyamic acid oligomer which is obtained by reacting an aromatic tetracarboxylic dianhydride including 2,2',3,3'-biphenyltetracarboxylic dianhydride, an aromatic diamine compound, and a terminal-crosslinking agent, and includes a crosslinkable group at the molecular terminal, a polyimide oligomer obtained by condensing the polyamic acid oligomer, a solution composition of the polyamic acid oligomer and/or the polyimide oligomer, and a fiber-reinforced composite material including the polyamic acid oligomer and/or the polyimide oligomer.

1. Polyimide Oligomer

Compounds used for synthesizing the polyimide oligomer of the present invention are described below.

1.1 Aromatic Tetracarboxylic Dianhydride 2,2',3,3'-Biphenyltetracarboxylic dianhydride is an essential component as the aromatic tetracarboxylic dianhydride. As examples of the aromatic tetracarboxylic dianhydride which may be used in combination, 3,3',4,4'-biphenyltetracarboxylic dianhydride (s-BPDA), 2,3,3',4'-biphenyltetracarboxylic dianhydride (a-BPDA), pyromellitic dianhydride (PMDA), 3,3',4,4'-benzophenonetetracarboxylic dianhydride (BTDA), 2,3,3',4'-benzophenonetetracarboxylic dianhydride (a-BTDA), diphenylsulfonetetracarboxylic dianhydride, oxydiphthalic dianhydride (ODPA), 2,2-bis(3,4-dicarboxyphenyl)hexafluoropropane dianhydride (6FDA), m-t-phenyl-3,4,3',4'-tetracarboxylic dianhydride, p-t-phenyl-3,4,3',4'-tetracarboxylic dianhydride, and 2,2-bis(3,4-dicarboxyphenyl)methane dianhydride can be given. In order to satisfy the relationship among heat resistance, mechanical properties, and processability, it is preferable to use 2,2',3,3'-biphenyltetracarboxylic dianhydride and at least one of 3,3',4,4'-biphenyltetracarboxylic dianhydride and 2,3,3',4'-biphenyltetracarboxylic dianhydride which are isomers of 2,2',3,3'-biphenyltetracarboxylic dianhydride. It is particularly preferable to use 2,3,3',4'-biphenyltetracarboxylic dianhydride in the presence of 2,2',3,3'-biphenyltetracarboxylic dianhydride from the viewpoint of maintaining the balance of required properties (heat resistance, mechanical properties, and processability).

The amount of 2,2',3,3'-biphenyltetracarboxylic dianhydride to be used is preferably 5 to 100 mol %, still more preferably 10 to 90 mol %, and particularly preferably 20 to 90 mol % of the total amount of the aromatic tetracarboxylic dianhydride.

In the case of using 2,3,3',4'-biphenyltetracarboxylic dianhydride in combination, the amount of 2,3,3',4'-biphenyltetracarboxylic dianhydride to be used is preferably 5 to 95 mol %, still more preferably 10 to 90 mol %, and particularly preferably 10 to 80 mol % of the total amount of the aromatic tetracarboxylic dianhydride.

1.2 Aromatic Diamine Compound

As examples of the aromatic diamine compound, p-phenylenediamine, m-phenylenediamine, 2,4-diaminotoluene, 4,4'-diaminodiphenylmethane, 4,4'-diamino diphenyl ether (4,4'-ODA), 3,4'-diamino diphenyl ether (3,4'-ODA), 3,3'-diamino diphenyl ether (3,3'-ODA), 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,7-diaminodimethyldibenzothiophene-5,5-dioxide, 4,4'-diaminobenzophenone, 3,3'-diaminobenzophenone, 4,4'-bis(4-aminophenyl)sulfide, 4,4'-diaminodiphenylsulfone, 4,4'-diaminobenzanilide, 1,n-bis(4-aminophenoxy)alkane, 1,3-bis[2-(4-aminophenoxyethoxy)]ethane, 9,9-bis(4-aminophenyl)fluorene, 9,9-bis(4-aminophenoxyphenyl)fluorene, 5(6)-amino-1-(4-aminomethyl)-1,3,3-trimethylindane, 1,4-bis(4-aminophenoxy)benzene (TPE-Q), 1,3-bis(4-aminophenoxy)benzene (TPE-R), 1,3-bis(3-aminophenoxy)benzene (APB), 2,5-bis(4-aminophenoxy)biphenyl (P-TPEQ), 4,4'-bis(4-aminophenoxy)biphenyl, 4,4'-bis(3-aminophenoxy)biphenyl, 2,2-bis(4-aminophenoxyphenyl)propane, 2,2-bis(4-aminophenoxyphenyl)hexafluoropropane, bis[4-(4-aminophenoxy)phenyl]sulfone, bis[4-(3-aminophenoxy)phenyl]sulfone, 2,2-bis[4-(4-aminophenoxy)phenyl]hexafluoropropane, benzidine, bis(2,2'-trifluoromethyl)benzidine, 1,3-bis(3-aminopropyl)-1,1,3,3-tetramethyldisiloxanne, 3,3-dimethoxy-4,4-diaminobiphenyl, 3,3-dimethyl-4,4-diaminobiphenyl, 2,2'-dichloro-4,4'-diamino-5,5'-dimethoxybiphenyl, 2,2',5,5'-tetrachloro-4,4'-diaminobiphenyl, 4,4'-methylene-bis(2-chloroaniline), 9,10-bis(4-aminophenyl)anthracene, and o-tolidinesulfone can be given. These compounds may be used individually or in combination of two or more. Of these, 4,4'-diamino diphenyl ether (4,4'-ODA), 2,5-bis(4-aminophenoxy)biphenyl (P-TPEQ), 3,4'-diamino diphenyl ether (3,4'-ODA), 1,3-bis(4-aminophenoxy)benzene (TPE-R), and 1,3-bis(3-aminophenoxy)benzene (APB) are preferable from the viewpoint of the resulting properties and processability.

1.3 Terminal-crosslinking Agent

A polyimide-precursor polyamic acid oligomer into which a crosslinkable group is introduced at the molecular terminal is obtained by reacting a terminal-crosslinking agent including a functional group which reacts with an amine or dicarboxylic anhydride and a crosslinkable group with at least either the aromatic tetracarboxylic dianhydride or the aromatic diamine compound.

The crosslinkable group has an unsaturated bond (double bond or triple bond), for example. Specifically, the terminal-crosslinking agent used in the present invention includes a group having an unsaturated bond. It is preferable that the group having an unsaturated bond include a functional group included in the monomer which can be used for synthesizing the polyimide (acid anhydride group or amino group, for example) from the viewpoint of reactivity at the time of introduction. Therefore, a polyimide-precursor polyamic acid oligomer into which a crosslinkable group having an unsaturated bond is introduced at the molecular terminal can be obtained by using the terminal-crosslinking agent including a group having an unsaturated bond.

As examples of the terminal-crosslinking agent including a group having a double bond, maleic anhydride, 5-norbornene-2,3-dicarboxylic anhydride, phthalic anhydride, vinylaniline, and p-aminostyrene can be given. This enables a polyimide-precursor polyamic acid oligomer into which a crosslinkable group having a double bond is introduced at the molecular terminal to be obtained. In the case of using maleic anhydride, maleic anhydride not only participates in polymerization, but also participates in an addition reaction together with the polyimide at the amine terminal.

As examples of the terminal-crosslinking agent including a group having a triple bond, propargylamine, ethynylaniline (such as 4-ethynylaniline and 3-ethynylaniline), phenylethynylaniline (such as 3-phenylethynylaniline), and phenylethynylphthalic anhydride (such as 4-(2-phenylethynyl)phthalic anhydride) can be given. This enables a polyimide-precursor polyamic acid oligomer into which a crosslinkable group having a triple bond is introduced at the molecular terminal to be obtained.

The terminal-crosslinking agent may be used either individually or in combination of two or more. However, it is preferable to individually use the terminal-crosslinking agent from the viewpoint of uniformly controlling the crosslinking density.

The amount (mol %) of the terminal-crosslinking agent such as phenylethynylphthalic anhydride which can react with an amine is specified by {(amount (mol %) of aromatic diamine compound)−(amount (mol %) of aromatic tetracarboxylic dianhydride)}×2.

In the case where the terminal-crosslinking agent includes a functional group which can react with an amine at the terminal, the amount of the terminal-crosslinking agent to be used is preferably 5 to 300 mol %, and still more preferably 5 to 200 mol % for the total amount of the aromatic tetracarboxylic dianhydride. In the case where the terminal-crosslinking agent includes a functional group which can react with an acid anhydride at the terminal, the amount of the terminal-crosslinking agent is preferably 5 to 200 mol %, and still more preferably 5 to 150 mol for the total amount of the aromatic diamine compound.

In the polyimide-precursor polyamic acid oligomer of the present invention, if the amount of the terminal-crosslinking agent is less than 5 mol % for the total amount of the aromatic diamine compound or the aromatic tetracarboxylic dianhydride, a large number of voids or bulges are formed on the surface of the cured product obtained from the resulting composition, whereby the mechanical properties may be significantly decreased. If the amount of the terminal-crosslinking agent exceeds 200 mol % for the total amount of the aromatic diamine compound, or the amount of the terminal-crosslinking agent exceeds 300 mol % for the total amount of the aromatic tetracarboxylic dianhydride, the crosslinking density of the resulting cured product increases, whereby the cured product becomes very fragile.

2. Method of Producing Polyimide Oligomer

The polyimide oligomer of the present invention is obtained by imidizing the polyimide-precursor polyamic acid oligomer by heating the polyamic acid oligomer to cause dehydration and cyclization to occur. This allows the polyimide oligomer of the present invention which includes a crosslinkable group at the molecular terminal to be obtained.

The reaction temperature when producing the polyimide-precursor polyamic acid oligomer is usually 0 to 80° C., and preferably 5 to 60° C. The reaction time is usually 0.5 to 48 hours, and preferably 1 to 24 hours.

As the method for imidizing the polyimide-precursor polyamic acid oligomer, i) a method of heating the polyamic acid oligomer at a temperature of 0 to 140° C. in the presence of an imidizing agent, and ii) a method of heating the polyamic acid oligomer at a temperature of 120 to 300° C. (preferably 150 to 250° C.) for 5 to 180 minutes can be given.

In the synthesis of the polyimide-precursor polyamic acid oligomer of the present invention, in the case where the aromatic diamine compound and the crosslinkable group have an amine structure, the amount of the aromatic tetracarboxylic dianhydride to be used is determined taking into consideration the total equivalent of amines including the amines in the aromatic diamine compound and the crosslinkable group. In the case where the aromatic tetracarboxylic dianhydride and the crosslinkable group have a carboxylic anhydride structure, the polyamic acid oligomer may be prepared in the above solvent according to a conventional polyimide synthesis method using the raw materials in an amount taking into consideration the total equivalent ratio of acid anhydrides including the acid anhydrides in the aromatic tetracarboxylic dianhydride and the crosslinkable group.

In order to securely introduce the crosslinkable group at the molecular terminal, it is preferable to prepare a terminal-reactive oligomer in advance using the raw materials excluding the terminal-crosslinking agent, and to react the terminal-crosslinking agent with the resulting terminal-reactive oligomer.

The molecular weight of the oligomer to be prepared may be adjusted by the equivalence ratio of the aromatic diamine compound to the aromatic tetracarboxylic dianhydride.

In the synthesis of the polyamic acid oligomer and the polyimide oligomer of the present invention, a solvent which can be used in conventional polyimide synthesis such as polyimide synthesis through polyamic acid may be used. For example, N,N-dimethylformamide, N,N-dimethylacetamide, sulfolane, N-methylpyrrolidone (NMP), γ-butyrolactone, phenol, or cresol may be used as the solvent. The solvent may be used either individually or in combination of two or more.

3. Properties of Polyimide Oligomer

3.1 Logarithmic Viscosity

The molecular weight of the polyamic acid oligomer of the present invention and the polyimide oligomer obtained by condensing the polyamic acid oligomer controls crosslinking density which dominates heat resistance and mechanical properties. The molecular weight of the polyamic acid oligomer and the polyimide oligomer of the present invention can be specified by logarithmic viscosity $\eta_{inh}$. The range of the logarithmic viscosity is preferably 0.03 to 0.5 dL/g (concentration: 0.5 g/dL, solvent: N-methylpyrrolidone (30° C.)), still more preferably 0.05 to 0.5 dL/g, and particularly preferably 0.05 to 0.4 dL/g. The logarithmic viscosity $\eta_{inh}$ is a value calculated using the following equation.

Logarithmic viscosity $\eta_{inh}$=ln(solution viscosity/solvent viscosity)/solution concentration 3.2 Minimum Melt Viscosity and Minimum Modulus of Elasticity When curing the polyimide oligomer of the present invention, the polyimide oligomer is caused to flow by heating and is thermally cured through the flow region. A decrease in melt viscosity due to an increase in temperature and an increase in viscosity due to the progress of crosslinking occur before the polyimide oligomer of the present invention is cured. The "minimum melt viscosity" used herein refers to the minimum viscosity at this time. Specifically, the polyimide oligomer of the present invention has a minimum melt viscosity at a temperature at which the polyimide oligomer has a minimum modulus of elasticity. The temperature at which the melt viscosity of the terminal-modified oligomer before curing becomes minimum and the melt viscosity at this temperature were measured using a dynamic spectrometer "RDSII" (manufactured by Rheometrics Scientific Inc., measurement condition: parallel plate, frequency: 1 Hz, temperature sweep measurement). The "minimum modulus of elasticity" refers to a minimum modulus of elasticity shown by temperature dependence of the dynamic storage modulus.

The polyimide oligomer of the present invention may have a minimum melt viscosity of 10 to 100,000 poise. The measurement temperature differs depending on the structure of each oligomer. A difference between the temperature at which the oligomer has a minimum melt viscosity and the temperature at which the curing reaction occurs is necessary.

3.3 Thermal Properties

The polyimide oligomer of the present invention after curing has a glass transition temperature of 300° C. or more and a flexural strength of 130 MPa or more.

4. Solution Composition

The solution composition of the present invention includes the polyamic acid oligomer and/or the polyimide oligomer of the present invention and an organic solvent. As the organic solvent, a solvent which can be used in the synthesis of the polyimide oligomer of the present invention may be used (see above "Method of producing polyimide oligomer" for specific solvents).

The polyamic acid oligomer and/or the polyimide oligomer in the solution composition of the present invention exhibits high solubility in the solvent, whereby the concentration in the solution composition can be adjusted to 20 wt % or more. If the concentration of the oligomer in the solution composition is high, occurrence of internal voids which cause dynamic defects when producing a composite material (described later) can be prevented, whereby a decrease in mechanical properties can be prevented. Moreover, since the concentration of the polyimide oligomer in the solution composition can be increased, the amount of resin with which fibers can be impregnated can be controlled. In the case of using the solution composition of the present invention for forming a prepreg, the concentration of the polyimide oligomer in the solution composition of the present invention is usually 20 wt % or more.

The solution composition of the present invention may further include short fibers, fillers, and the like depending on the objective. As examples of the fillers, oxides such as a silicate and silicate nitride, nonoxides such as silicon nitride and silicon carbide, and powdered substances such as graphite and Teflon (registered trademark) can be given.

5. Fiber-reinforced Composite Material

The fiber-reinforced composite material of the present invention can be obtained by thermally curing a prepreg in which a fibrous reinforcement material is impregnated with an organic solvent solution of the polyimide oligomer of the present invention.

There are no specific limitations to the fibrous reinforcement material. As examples of the fibrous reinforcement material, polyazole fiber, polyacrylonitrile-based carbon fiber, pitch-based carbon fiber, aramid fiber, glass fiber, alumina fiber, silicone carbide fiber, Si—Ti—C—O fiber (manufactured by Ube Industries, Ltd.; Tyranno fiber), and the like can be given. The fiber may be used either individually or in combination of two or more. The reinforcement fiber may be provided with a conventional surface treatment (sizing treatment, for example). In the case where the fibrous reinforcement material is carbon fiber, the fiber-reinforced composite material of the present invention may be an advanced composite material.

An example of the method of manufacturing the fiber-reinforced composite material from a prepreg formed using the polyimide oligomer of the present invention is described below. A prepreg is formed (laid up) by impregnating the fibrous reinforcement material with the polyimide oligomer of the present invention. The resulting prepregs are stacked in layers by using a conventional method (reduced-pressure bag/autoclave curing method, hotpress method, or sheet winding method, for example) to form a stacked product. The stacked product is molded by heating the stacked product at a temperature of 200 to 500° C. and a pressure of about 3 to 1000 kg/cm². The fiber-reinforced composite material of the present invention is thus obtained.

In this method, the prepreg may be laid up at a temperature of usually 30 to 300° C., and preferably 100 to 275° C. If the prepreg is laid up in this temperature range, the resulting prepreg exhibits tuck properties and drape properties, whereby excellent workability is achieved.

The content of the fibrous reinforcement material in the fiber-reinforced composite material of the present invention (fiber content by volume) is 20 to 80 vol %, and preferably 30 to 75 vol %.

Since the polyimide oligomer of the present invention has a glass transition temperature of 300° C. or more and a flexural strength of 130 MPa or more, the fiber-reinforced composite material of the present invention including the polyimide oligomer exhibits excellent heat resistance. Moreover, since the fiber-reinforced composite material is reinforced by the fibrous reinforcement material, the fiber-reinforced composite material has excellent mechanical strength.

6. Other Applications

The polyimide oligomer of the present invention may be used not only for producing the fiber-reinforced composite material, but also as a functional material such as an insulating material and a heat-resistant adhesive for bonding metal foil.

In the case of using the polyimide oligomer of the present invention as a molding material resin, a polyimide is obtained without thermally curing the polyimide oligomer of the present invention. The polyimide is optionally purified by separation and then powdered. A molded product can be formed by using the polyimide powder. As the molding method, a conventional method such as a press molding method, a transfer molding method, or an injection molding method may be applied.

(4,4'-diamino diphenyl ether; hereinafter abbreviated as "ODA"). After the addition of 40 mL of N,N-dimethylacetamide (hereinafter abbreviated as "DMAc") which was dehydrated and purified by distillation, ODA was dissolved with stirring. After the addition of 2.942 g (0.020 mol) of sufficiently dried 2,2',3,3'-biphenyltetracarboxylic dianhydride (hereinafter abbreviated as "i-BPDA") in powdery form to the reaction system, the mixture was polymerized at room temperature for one hour. After the addition of 4.965 g (0.020 mol) of 4-phenylethynylphthalic anhydride (hereinafter abbreviated as "PEPA") in powdery form as the terminal-crosslinking agent, the mixture was allowed to react at room temperature for one hour to obtain a polyamic acid oligomer. The calculated value of the repeating unit n of the oligomer in this example shown by the following formula (1) is 1.5. The logarithmic viscosity $\eta_{inh}$ was 0.04 dL/g.

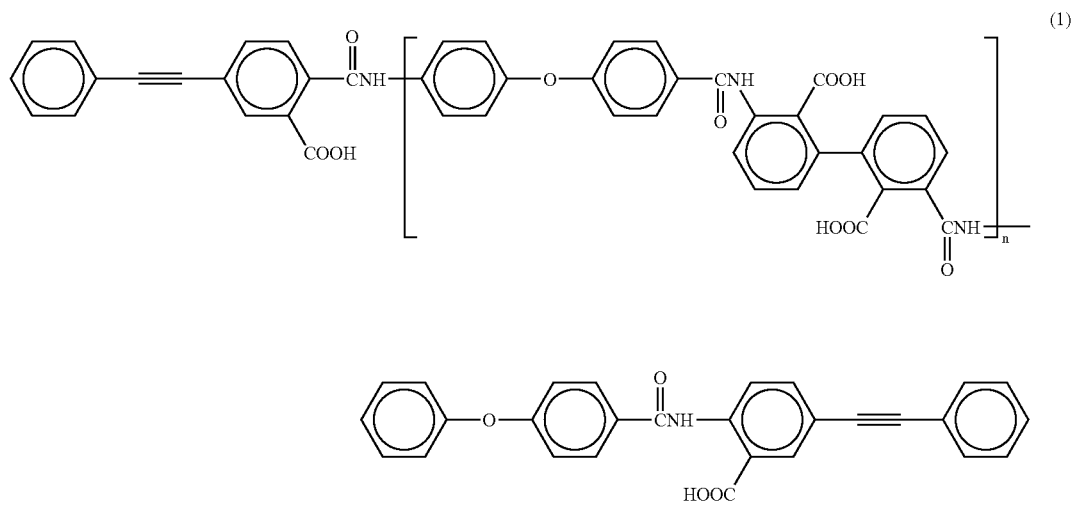

(1)

7. EXAMPLES

The present invention is described below in more detail based on examples. However, the present invention is not limited to the following examples. The evaluation items in each example were measured as described below.

Measurement of Glass Transition Temperature (Tg)

The glass transition temperature was measured at a temperature rising rate of 0.5° C./min in a nitrogen atmosphere using a dynamic mechanical analyzer (DMA).

Pyrolysis Temperature

The pyrolysis temperature was measured at a temperature rising rate of 20° C./min in a nitrogen atmosphere using thermal gravimetric analysis (TGA). The 5% weight loss temperature was employed as the pyrolysis temperature $Td_{5\%}$.

Flexural Modulus of Elasticity and Flexural Strength

The flexural modulus of elasticity and flexural strength were measured according to ASTM D-790.

7.1 Example 1

A reaction vessel equipped with an electromagnetic stirrer was charged with 4.005 g (0.020 mol) of oxydianiline The polymerization solution of the resulting polyamic acid oligomer was applied to a glass plate, and dried at 60° C. for one hour and at 150° C. for one hour. The dried product was subjected to a heat treatment in a vacuum drier at 200° C. for half an hour and at 250° C. for one hour. A polyimide oligomer shown by the following formula (2) was obtained by this step. The maximum solubility of the polyimide oligomer in NMP (maximum dissolution concentration) was 25 to 30 wt %. The resulting polyimide oligomer was ground into powder using a mortar. The powder was compressed and thermally formed at a temperature of 370° C. and a pressure of 5 MPa for one hour to obtain a thin piece (cured test specimen).

Thermal properties, processability, and strength properties of the cured test specimen were examined. The glass transition temperature of the test specimen was 337° C. The temperature at which the test specimen had a minimum melt viscosity, which is an index of processability, was 425° C. The modulus of elasticity at the temperature at which the test specimen had a minimum melt viscosity (minimum modulus of elasticity, that is, minimum modulus of elasticity indicated by temperature dependence of dynamic storage modulus) was 50 MPa.

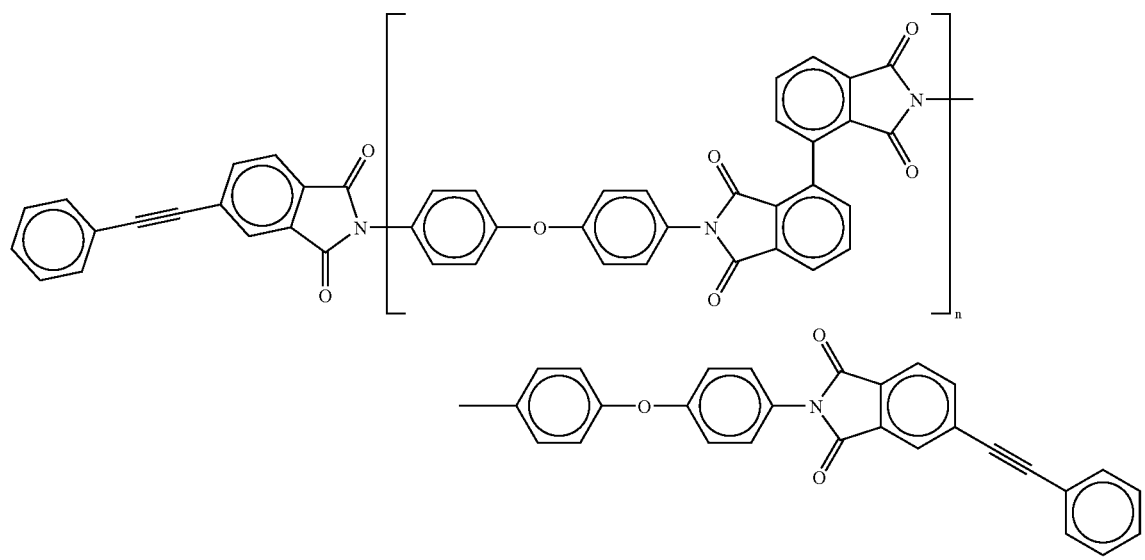

(2)

7.2 Examples 2 and 3

Operations and processing were performed in the same manner as in Example 1 except for changing the composition of the monomers and the terminal-crosslinking agent as shown in Table 1 to prepare a cured test specimen. The results are shown in Table 2.

7.3 Comparative Example 1

Instead of the aromatic tetracarboxylic anhydride (i-BPDA) used in Example 2, 3,3',4,4'-biphenyltetracarboxylic dianhydride (hereinafter abbreviated as "s-BPDA"), which is an isomer of i-BPDA, was used. The evaluation results are shown in Table 3.

7.4 Comparative Example 2

Instead of the aromatic tetracarboxylic anhydride (i-BPDA) used in Example 2, 2,3,3',4'-biphenyltetracarboxylic dianhydride (hereinafter abbreviated as "a-BPDA"), which is an isomer of i-BPDA, was used. The evaluation results are shown in Table 3.

TABLE 1

| Example | Aromatic tetracarboxylic dianhydride Monomer i-BPDA Amount (g) | (mol) | Aromatic diamine compound Monomer 4,4'-ODA Amount (g) | (mol) | Terminal-crosslinking agent PEPA Amount (g) | (mol) | Repeating unit n (calculated value) | Logarithmic viscosity $\eta_{inh}$ (dL/g) |
|---|---|---|---|---|---|---|---|---|
| 1 | 2.942 | 0.01 | 4.005 | 0.02 | 4.965 | 0.02 | 1.5 | 0.04 |
| 2 | 11.769 | 0.04 | 10.012 | 0.05 | 4.965 | 0.02 | 4 | 0.09 |
| 3 | 10.592 | 0.036 | 8.001 | 0.04 | 1.986 | 0.008 | 9 | 0.15 |

TABLE 2

| Example | Maximum dissolution concentration (NMP) (wt %) | Processability | | | Properties of cured product | | | | |
| | | Minimum melt viscosity (poise) | Minimum melt viscosity temperature (° C.) | Minimum modulus of elasticity (MPa) | Tg (DMA) (° C.) | $Td_{5\%}$ (TGA) (° C.) | Flexural modulus of elasticity (GPa) | Flexural strength (MPa) | Elongation (%) |
|---|---|---|---|---|---|---|---|---|---|
| 1 | 25–30 | 350 | 425 | 50 | 337 | 524 | 2.4 | 215 | 3 |
| 2 | 25–30 | 800 | 400 | 4 | 335 | 520 | 2.1 | 185 | 8 |
| 3 | 25–30 | 12000 | 440 | 3 | 327 | 527 | 1.8 | 180 | 10 |

TABLE 3

| Comparative Example | Maximum dissolution concentration (NMP) (wt %) | Processability | | | Properties of cured product | | | | |
|---|---|---|---|---|---|---|---|---|---|
| | | Minimum melt viscosity (poise) | Minimum melt viscosity temperature (° C.) | Minimum modulus of elasticity (MPa) | Tg (DMA) (° C.) | Td$_{5\%}$ (TGA) (° C.) | Flexural modulus of elasticity (GPa) | Flexural strength (MPa) | Elongation (%) |
| 1 | ≦10 | 2800 | 385 | 75 | 284 | 527 | 2.8 | 140 | 10 |
| 2 | ≦15 | 700 | 395 | 4 | 343 | 530 | 2.2 | 160 | 10 |

7.5 Examples 4 to 8

A mixture of i-BPDA and s-BPDA was used as the aromatic tetracarboxylic dianhydride instead of independently using the aromatic tetracarboxylic dianhydride (i-BPDA) in Example 2. The composition of the monomers and the terminal-crosslinking agent is shown in Table 4. Operations and processing were performed in the same manner as in Example 1 to prepare a cured test specimen. The results are shown in Table 5.

TABLE 4

| | Aromatic tetracarboxylic dianhydride | | | | | Aromatic diamine | | Terminal-crosslinking agent | | | |
|---|---|---|---|---|---|---|---|---|---|---|---|
| | Monomer i-BPDA Amount | | Monomer s-BPDA Amount | | i/a composition ratio | compound Monomer 4,4'-ODA Amount | | agent PEPA Amount | | Repeating unit n (calculated value) | Logarithmic viscosity $\eta_{inh}$ (dL/g) |
| Example | (g) | (mol) | (g) | (mol) | | (g) | (mol) | (g) | (mol) | | |
| 4 | 1.177 | 0.004 | 4.708 | 0.016 | 20/80 | 5.006 | 0.025 | 2.482 | 0.01 | 4 | 0.10 |
| 5 | 1.177 | 0.006 | 4.119 | 0.014 | 30/70 | 5.006 | 0.025 | 2.482 | 0.01 | 4 | 0.09 |
| 6 | 2.942 | 0.010 | 2.942 | 0.010 | 50/50 | 5.006 | 0.025 | 2.482 | 0.01 | 4 | 0.11 |
| 7 | 4.119 | 0.014 | 1.765 | 0.006 | 70/30 | 5.006 | 0.025 | 2.482 | 0.01 | 4 | 0.12 |
| 8 | 5.296 | 0.018 | 0.588 | 0.002 | 90/10 | 5.006 | 0.025 | 2.482 | 0.01 | 4 | 0.11 |

TABLE 5

| Example | Maximum dissolution concentration (NMP) (wt %) | Processability | | | Properties of cured product | | | | |
|---|---|---|---|---|---|---|---|---|---|
| | | Minimum melt viscosity (poise) | Minimum melt viscosity temperature (° C.) | Minimum modulus of elasticity (MPa) | Tg (DMA) (° C.) | Td$_{5\%}$ (TGA) (° C.) | Flexural modulus of elasticity (GPa) | Flexural strength (MPa) | Elongation (%) |
| 4 | ≧40 | 850 | 400 | 5 | 304 | 528 | 2.7 | 165 | 13 |
| 5 | ≧40 | 700 | 430 | 4 | 329 | 534 | 2.7 | 165 | 12 |
| 6 | ≧40 | 780 | 420 | 4 | 339 | 531 | 2.5 | 170 | 13 |
| 7 | ≧40 | 900 | 400 | 5 | 331 | 529 | 2.4 | 160 | 9 |
| 8 | ≧40 | 840 | 410 | 7 | 329 | 538 | 2.3 | 160 | 8 |

7.6 Examples 9 to 11 a-BPDA, which is an isomer of s-BPDA, was used instead of s-BPDA in the mixture of i-BPDA and s-BPDA used as the aromatic tetracarboxylic dianhydride in Examples 4 to 8. The polymerization formulation in Examples 9 to 11 is shown in Table 6. DMAc was used as the polymerization solvent in the same manner as in other examples. DMAc was used in an amount of 55 mL. Operations and processing were performed in the same manner as in Example 1 to prepare a cured test specimen. The results are shown in Table 7.

TABLE 6

| Example | Aromatic tetracarboxylic dianhydride | | | | i/a composition ratio | Aromatic diamine compound Monomer 4,4'-ODA | | Terminal-crosslinking agent PEPA | | Repeating unit n (calculated value) | Logarithmic viscosity $\eta_{inh}$ (dL/g) |
|---|---|---|---|---|---|---|---|---|---|---|---|
| | Monomer i-BPDA Amount (g) | (mol) | Monomer a-BPDA Amount (g) | (mol) | | Amount (g) | (mol) | Amount (g) | (mol) | | |
| 9 | 2.942 | 0.01 | 8.8266 | 0.03 | 25/75 | 10.012 | 0.05 | 0.02 | 4.965 | 4 | 0.10 |
| 10 | 5.884 | 0.02 | 5.884 | 0.02 | 50/50 | 10.012 | 0.05 | 0.02 | 4.965 | 4 | 0.11 |
| 11 | 8.827 | 0.03 | 2.942 | 0.01 | 75/25 | 10.012 | 0.05 | 0.02 | 4.965 | 4 | 0.11 |

TABLE 7

| Example | Maximum dissolution concentration (NMP) (wt %) | Processability | | | Properties of cured product | | | | |
|---|---|---|---|---|---|---|---|---|---|
| | | Minimum melt viscosity (poise) | Minimum melt viscosity temperature (° C.) | Minimum Modulus of elasticity (MPa) | Tg (DMA) (° C.) | Td$_{5\%}$ (TGA) (° C.) | Flexural modulus of elasticity (GPa) | Flexural strength (MPa) | Elongation (%) |
| 9 | ≧50 | 1100 | 430 | 5 | 323 | 518 | 2.5 | 164 | 10 |
| 10 | ≧40 | 1200 | 420 | 6 | 329 | 530 | 2.6 | 148 | 9 |
| 11 | ≧40 | 1300 | 420 | 7 | 318 | 517 | 2.6 | 153 | 7 |

7.7 Comparative Examples 3 to 5 a-BPDA was used instead of i-BPDA used in Examples 4, 6, and 7. The method for polymerization, processing, and molding was according to Examples 4, 6, and 7 to prepare a cured test specimen. The resulting test specimen was evaluated. The results are shown in Table 8.

TABLE 8

| Comparative Example | a/s composition ratio | Processability | | | | Properties of cured product | | | | |
|---|---|---|---|---|---|---|---|---|---|---|
| | | Maximum dissolution concentration (NMP) (wt %) | Minimum melt viscosity (poise) | Minimum melt viscosity temperature (° C.) | Minimum modulus of elasticity (MPa) | Tg (DMA) (° C.) | Td$_{5\%}$ (TGA) (° C.) | Flexural modulus of elasticity (GPa) | Flexural strength (MPa) | Elongation (%) |
| 3 | 20/80 | ≦15 | 1500 | 385 | 10 | 295 | 526 | 2.5 | 145 | 12 |
| 4 | 50/50 | ≦15 | 1200 | 395 | 8 | 310 | 534 | 3.2 | 152 | 10 |
| 5 | 70/30 | ≦15 | 1400 | 415 | 7 | 305 | 531 | 2.8 | 157 | 6 |

7.8 Examples 12 to 15

A mixture of 4,4'-diamino diphenyl ether (ODA) and bis(2,4-(4-aminophenoxy))biphenyl (PTPEQ) was used as the aromatic diamine compound instead of independently using ODA in Example 1. The polymerization formulation in Examples 12–15 is shown in Table 9. DMAc was used as the polymerization solvent in the same manner as in other examples. DMAc was used in an amount of 55 mL. Operations and processing were performed in the same manner as in Example 1 to prepare a cured test specimen. The results are shown in Table 10.

TABLE 9

| | Aromatic tetracarboxylic dianhydride Monomer | | Aromatic diamine compound Monomer | | | | Terminal-crosslinking agent | | Repeating unit n (calculated value) | Logarithmic viscosity $\eta_{inh}$ (dL/g) |
|---|---|---|---|---|---|---|---|---|---|---|
| | i-BPDA Amount | | 4,4'-ODA Amount | | P-TPEQ Amount | | PEPA Amount | | | |
| Example | (g) | (mol) | (g) | (mol) | (g) | (mol) | (g) | (mol) | | |
| 12 | 11.7688 | 0.04 | 9.0099 | 0.045 | 1.8421 | 0.005 | 4.9648 | 0.02 | 4 | 0.11 |
| 13 | 11.7688 | 0.04 | 8.0096 | 0.040 | 3.6842 | 0.010 | 4.9648 | 0.02 | 4 | 0.13 |
| 14 | 11.7688 | 0.04 | 6.0072 | 0.030 | 7.3684 | 0.020 | 4.9648 | 0.02 | 4 | 0.12 |
| 15 | 11.7688 | 0.04 | 4.0048 | 0.020 | 11.0526 | 0.030 | 4.9648 | 0.02 | 4 | 0.16 |

TABLE 10

| | Maximum dissolution concentration (NMP) (wt %) | Processability | | | Properties of cured product | | | | |
|---|---|---|---|---|---|---|---|---|---|
| | | Minimum melt viscosity (poise) | Minimum melt viscosity temperature (° C.) | Minimum modulus of elasticity (MPa) | Tg (DMA) (° C.) | $Td_{5\%}$ (TGA) (° C.) | Flexural modulus of elasticity (GPa) | Flexural strength (MPa) | Elongation (%) |
| Example | | | | | | | | | |
| 12 | ≦40 | 1800 | 370 | 9 | 306 | 522 | 2.5 | 150 | 9 |
| 13 | ≦40 | 1400 | 365 | 8 | 308 | 526 | 2.6 | 164 | 9 |
| 14 | ≦40 | 1900 | 380 | 8 | 305 | 528 | 2.8 | 160 | 11 |
| 15 | ≦40 | 1600 | 385 | 7 | 302 | 520 | 2.8 | 153 | 10 |

7.9 Example 16

A polyimide oligomer solution (DMAc solution, solid content: 50%) was obtained by using the same method as in Example 9. The resulting solution was used as an impregnation solution. Carbon fibers (Besfight HTS3000 manufactured by Toho Rayon Co., Ltd.) were impregnated with the impregnation solution at a humidity of 50% and a temperature of 25° C., and wound using a drum winder. The carbon fibers were aligned in one direction, and dried at 100° C. for 30 minutes. The dried product was subjected to imidization at 270° C. for 30 minutes in nitrogen stream to prepare a composite material.

The composite material (thickness: 150 μm) was cut into squares at a dimension of 150 mm. Eight squares were layered in the same direction, pressed at 380° C. and 20 kg/cm² for 30 minutes, and cooled to 100° C. while maintaining the pressure to obtain a sheet formed of the fiber-reinforced composite material of this example. A test specimen was cut from the resulting sheet, and subjected to measurement of flexural strength and flexural modulus of elasticity according to ASTM D-790. The volume void content of the sheet was also measured. The volume void content was calculated from the specific gravity and the fiber content by weight of the sheet. The results are given below.

Flexural modulus of elasticity: 145 GPa
Flexural strength: 2.6 GPa
Fiber content by volume: 60%
Volume void content: 0%

According to the present invention, a polyamic acid oligomer having 1) heat resistance (high Tg of 300° C. or more), 2) toughness, and 3) excellent solubility in a solvent, and a polyimide oligomer obtained from the polyamic acid oligomer can be provided. Specifically, the polyamic acid oligomer and the polyimide oligomer of the present invention are useful as a molding material such as a matrix resin of a composite material used under a severe heat resistant environment, such as instruments for airplanes, space industries, and automobiles, and as a functional material such as an insulating material and a heat-resistant adhesive.

The polyamic acid oligomer and/or the polyimide oligomer of the present invention may be dissolved in an organic solvent and utilized as a solution composition.

The fiber-reinforced composite material obtained by thermally curing a prepreg in which a fibrous reinforcement material is impregnated with an organic solvent solution of the polyamic acid oligomer and/or the polyimide oligomer of the present invention has heat resistance and toughness.

What is claimed is:

1. A polyamic acid oligomer which is obtained by reacting an aromatic tetracarboxylic dianhydride including 2,2',3,3'-biphenyltetracarboxylic dianhydride, an aromatic diamine compound, and a terminal-crosslinking agent, and includes a crosslinkable group at a molecular terminal.

2. The polyamic acid oligomer as defined in claim 1, wherein the aromatic tetracarboxylic dianhydride further includes 3,3',4,4'-biphenyltetracarboxylic dianhydride and/or 2,3,3',4'-biphenyltetracarboxylic dianhydride.

3. The polyamic acid oligomer as defined in claim 1, having a logarithmic viscosity ($\eta_{inh}$) (concentration: 0.5 g/dL, solvent: N-methylpyrrolidone (30° C.)) of 0.03 to 0.5 dL/g.

4. The polyamic acid oligomer as defined in claim 1, having a minimum melt viscosity of 10 to 100,000 poise.

5. The polyamic acid oligomer as defined in claim 1, wherein the terminal-crosslinking agent is at least one compound selected from the group consisting of vinylaniline, aminostyrene, ethynylaniline, phenylethynylaniline, propargylamine, maleic anhydride, 5-norbornene-2,3-dicarboxylic anhydride, and phenylethynylphthalic anhydride.

6. The polyamic acid oligomer as defined in claim 1, having a glass transition temperature of 300° C. or more and a flexural strength of 130 MPa or more after curing.

7. A polyimide oligomer which is obtained by condensing the polyamic acid oligomer as defined in claim 1, the polyamic acid oligomer having a logarithmic viscosity ($\eta_{inh}$) (concentration: 0.5 g/dL, solvent: N-methylpyrrolidone (30° C.)) of 0.03 to 0.5 dL/g.

8. A solution composition comprising:
a polyamic acid oligomer which is obtained by reacting an aromatic tetracarboxylic dianhydride including 2,2',3,3'-biphenyltetracarboxylic dianhydride, an aromatic diamine compound, and a terminal-crosslinking agent, and includes a crosslinkable group at a molecular terminal; and/or
a polyimide oligomer which is obtained by condensing the polyamic acid oligomer, the polyamic acid oligomer having a logarithmic viscosity ($\eta_{inh}$) (concentration: 0.5 g/dL, solvent: N-methylpyrrolidone (30° C.)) of 0.03 to 0.5 dL/g; and
an organic solvent.

9. The solution composition as defined in claim 8, wherein the concentration of the polyamic acid oligomer and/or the polyimide oligomer is 20 wt % or more.

10. A fiber-reinforced composite material obtained by thermally curing a prepreg in which a fibrous reinforcement material is impregnated with an organic solvent solution of:
a polyamic acid oligomer which is obtained by reacting an aromatic tetracarboxylic dianhydride including 2,2',3,3'-biphenyltetracarboxylic dianhydride, an aromatic diamine compound, and a terminal-crosslinking agent, and includes a crosslinkable group at a molecular terminal; and/or
a polyimide oligomer which is obtained by condensing the polyamic acid oligomer, the polyamic acid oligomer having a logarithmic viscosity ($\eta_{inh}$) (concentration: 0.5 g/dL, solvent: N-methylpyrrolidone (30° C.)) of 0.03 to 0.5 dL/g.

11. The fiber-reinforced composite material as defined in claim 10, wherein the fibrous reinforcement material is carbon fiber.

* * * * *